United States Patent [19]
Takeda

[11] Patent Number: 5,221,517
[45] Date of Patent: Jun. 22, 1993

[54] METHANE ANALYZER WITH IMPROVED SAMPLE PREPARATION

[75] Inventor: Kenji Takeda, Kyogo, Japan
[73] Assignee: Horiba, Ltd., Kyoto, Japan
[21] Appl. No.: 974,150
[22] Filed: Nov. 10, 1992
[30] Foreign Application Priority Data
  Dec. 17, 1991 [JP] Japan .................. 3-110741[U]
[51] Int. Cl.$^5$ .................................. G01N 31/12
[52] U.S. Cl. .................................. 422/54; 422/83;
    422/93; 422/94; 73/23.2; 73/23.31; 73/23.32
[58] Field of Search ............. 422/83, 93, 54, 94;
    73/23.2, 23.31, 23.32

[56] References Cited
U.S. PATENT DOCUMENTS

| | | | |
|---|---|---|---|
| 3,340,013 | 9/1967 | Rooney et al. | 422/90 |
| 4,063,895 | 12/1977 | Neti et al. | 422/91 |
| 4,167,334 | 9/1979 | Phillips | 356/315 |
| 4,705,669 | 11/1987 | Tsuj et al. | 422/93 |
| 4,755,357 | 7/1988 | Noguchi et al. | 422/103 |
| 4,814,143 | 3/1989 | Kojima et al. | 422/83 |
| 5,041,265 | 8/1991 | Koike et al. | 422/94 |

FOREIGN PATENT DOCUMENTS
62-8524 2/1987 Japan .

Primary Examiner—James C. Housel
Assistant Examiner—N. Bhat
Attorney, Agent, or Firm—Price, Gess & Ubell

[57] ABSTRACT

A methane analyzer system having a cutter for preparing a sample gas prior to submission to a hydrogen flame ionization detector includes a source dilution gas that is connected to the hydrogen flame ionization detector, and a flow restrictor line for directing a portion of the dilution gas to the cutter for mixing with the sample gas prior to introduction into the ionization detector. A source of fuel, such as hydrogen, which is connected to the ionization detector, is also metered in measured quantities to the cutter to stabilize the oxidation of the sample gas.

11 Claims, 1 Drawing Sheet

METHANE ANALYZER WITH IMPROVED SAMPLE PREPARATION

BACKGROUND OF THE INVENTION

1. Field of the Invention

The present invention relates to a methane analyzer using a so-called cutter method in which a cutter chamber removes those hydrocarbons other than methane (hereinafter referred to as "nonmethane hydrocarbons") contained in a sample gas as a preliminary process step of a hydrogen flame ionization detector system (hereinafter referred to as "FID") and, more particularly, to a controlled dilution of the sample gas prior to submission to the hydrogen flame ionization detector.

2. Description of Related Art

In a methane analyzer, as disclosed, for example, in Japanese Utility Model Publication No. Sho 62-8524, a cutter chamber can be provided in a prestage or first portion of an FID, and an oxygen gas passageway can be provided with a flow rate regulator connected with the cutter chamber to supply oxygen to the cutter, whereby the process step of burning (oxidizing) the nonmethane hydrocarbons, contained in a sample gas, is used to remove them, followed by burning the sample gas, from which said nonmethane hydrocarbons have been removed, in the FID.

It is, however, necessary to keep the concentration of oxygen supplied to the cutter at an appointed or greater value (for example, 15% by volume or more) in order to burn the nonmethane hydrocarbons in the cutter chamber. Accordingly, a CVS dilution measuring method, in which an exhaust gas as a sample gas is diluted with air, has been used in order to analyze an exhaust gas from motorcars by a methane analyzer of this type. Thus, methane has been unable to be measured directly without diluting the exhaust gas.

In addition, in a methane analyzer as disclosed in Japanese Utility Model Publication No. Sho 62-8524, it is also necessary to provide an oxygen cylinder separately from the air supplied as the operating air for the FID. Thus, disadvantages have occurred in that the methane analyzer of this type is further complicated in construction and expensive.

Thus, the prior art is still seeking to provide an improved methane analyzer system.

SUMMARY OF THE INVENTION

The present invention is directed to the above-described matters, and it is an object of the present invention to provide a relatively inexpensive methane analyzer capable of measuring a sample gas, not only after being diluted, but also in a manner that is both direct and simple in construction.

In order to achieve the above-described object, a portion of an operating air source which is supplied to an FID is also supplied to a cutter through a flow rate regulator system.

The sample gas can be diluted at a predetermined ratio by supplying the cutter chamber, for removing nonmethane hydrocarbons contained in the sample gas, with a portion of the operating air supplied to the FID. Accordingly, a direct measurement can be achieved. In addition, since the air used for dilution is also a part of the operating air supplied to the FID, it is not necessary to provide a separate source of diluting air. Thus, the methane analyzer can be both simple in construction and inexpensive.

An improved methane analyzer system includes a supply line adapted to be connected to a sample gas, such as a motor exhaust, a source of oxygen, a source of fuel, and a cutter chamber connected to the sample gas supply line. A hydrogen flame ionization detector is connected to, respectively, the cutter, the source of oxygen, and the source of fuel. A pair of passageways is provided for directing a portion of the oxygen from the oxygen source to the cutter for dilution of the sample gas and for directing a portion of the fuel from the fuel source to the cutter to stabilize the oxidation of the sample gas by the cutter. A pressure valve and flow restrictor are used for regulating the flow of oxygen from the source of oxygen upstream from the passageway and the hydrogen flame ionization detector, whereby a correct portion of oxygen is finally delivered to the hydrogen flame ionization detector directly from the source of oxygen and indirectly through a dilution of the sample gas in the cutter. Another pressure valve and flow restrictor regulates the flow of fuel from the source of fuel upstream from both the passageway and the hydrogen flame ionization detector, whereby a correct portion of fuel is finally delivered to the hydrogen flame ionization detector directly from the source of fuel and indirectly through the cutter.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

Figure 1:
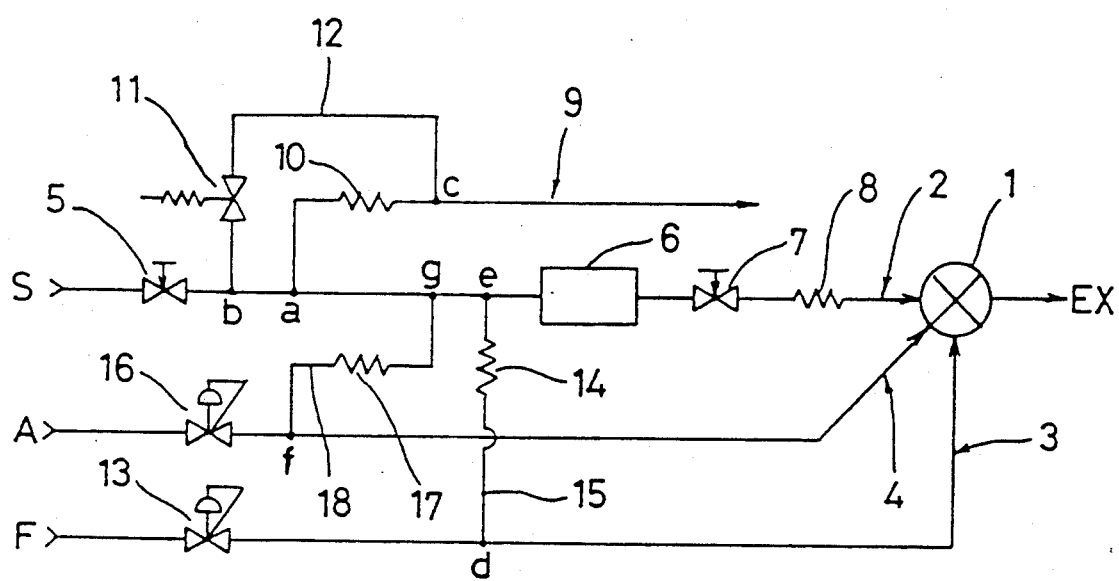
FIG. 1 is a schematic drawing showing one preferred embodiment of a methane analyzer system according to the present invention.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an improved methane analyzer system for preparation of a diluted sample gas in an efficient manner.

FIG. 1 schematically shows a construction of a methane analyzer system according to the present invention. Referring to FIG. 1, reference numeral 1 designates a known FID structure. A sample gas-supplying pipe 2 for supplying a sample gas S, an operating fuel-supplying pipe 3 for supplying an operating fuel F (for example, hydrogen gas), and an operating air-supplying pipe 4 for supplying operating air A are connected with the FDI 1.

The sample gas-supplying pipe 2 is connected with a sample gas-supplying source (not shown) on the upstream side thereof, e.g., a motor exhaust. The sample gas-supplying pipe 2 is provided with a flow rate-regulating valve 5, a cutter 6, a fine regulation valve 7, and a flow rate-regulating capillary or flow restrictor 8 in the order described from the upstream side thereof. The flow rate-regulating valve 5 provides a suitable regulation of a flow rate of the sample gas S from the sample gas-supplying source and, for example, a needle valve can be used as the flow rate-regulating valve 5. The purpose of the cutter 6 is to permit removal of nonmethane hydrocarbons contained in the sample gas S and includes an oxidizing catalyst contained in a reaction chamber, such as oxides of copper and manganese, platinum, palladium, and Popcalite ™, approximately positioned in an inside chamber thereof. The fine regulation valve 7 provides a fine regulation of the sample gas flow rate, which can fluctuate by passage of the sample gas S through the cutter 6. For example, a needle valve can be used as the fine regulation valve 7.

The sample gas-supplying pipe 2 is provided with, for example, a bypass pipe 9 opened to ambient air at the other end and connected therewith at a point (a) between the flow rate-regulating valve 5 and the cutter 6. The bypass pipe 9 provides a discharge of any overflow sample gas S, and is also provided with a flow controller (for example, a capillary flow restrictor 10. In addition, the sample gas-supplying pipe 2 is also provided with a pipe 12 provided with a pressure regulator 11 so as to connect a point (b) between the flow rate-regulating valve 5, and the point (a) with a point (c) on the downstream side of the flow controller 10 in the bypass pipe 9, thereby regulating the pressure of the sample gas S.

The operating fuel-supplying pipe 3 is connected with a fuel source (not shown) (in this case a hydrogen cylinder) on the upstream side thereof. The operating fuel-supplying pipe 3 is provided with a regulator 13. The operating fuel-supplying pipe 3 is further provided with a pipe 15, which is also provided with a flow controller (for example, a capillary flow restrictor) 14 so as to connect a point (d) on the downstream side of the regulator 13 with a point (e) between the point (a) and the cutter 6 in the sample gas-supplying pipe 2, thereby supplying the cutter 6 with a fuel gas such as hydrogen gas.

The operating air-supplying pipe 4 is connected with an air cylinder or oxygen cylinder (not shown). The operating air-supplying pipe 4 is provided with a regulator 16. The operating air-supplying pipe 4 is further provided with a bypass pipe 18 having a flow controller (for example, a capillary flow restrictor) 17 so as to connect a point (f) on the downstream side of the regulator 16 therein with a point (g) (a point on the upstream side of the point (e)) between the point (a) and the cutter 6 in the sample gas-supplying pipe 2, thereby supplying the cutter 6 with a portion of the same operating air A being supplied to the FID 1. The flow rate of the air being supplied to the cutter 6 is set by means of the flow controllers 10, 14.

In addition, in the above-described construction, air in the atmosphere may be refined and pressurized to provide an air source in place of an air cylinder.

Next, the operation of the methane analyzer system having the above-described construction will be described. At first, in a direct measurement process, in which the nondiluted sample gas S is measured, the nondiluted sample gas (raw sample gas) S from a sample gas-supplying source (not shown) (for example, an engine of a motorcar) is connected and supplied to the sample gas-supplying pipe 2. At the same time, hydrogen gas F from a fuel source (not shown) is supplied to the operating fuel-supplying pipe 3, and the operating air A from the air cylinder (not shown) is supplied to the air-supplying pipe 4.

The raw sample gas S is supplied to the cutter 6 at an appointed flow rate and pressure through the flow-rate controlling valve 5. At this time, any excessive raw sample gas S is discharged through the bypass pipe 9. The hydrogen gas F as the operating fuel and the operating air A are regulated to an appointed pressure by means of the respective regulators 13 and 16, and then supplied to the FDI 1, and a part of these gases is supplied to the cutter 6 through the flow controllers 14, 17, respectively. As can be appreciated, the control of these regulators can be made automatic with a microprocessor-based system and appropriate pressure sensors In the cutter 6, the raw sample gas S is diluted by, for example, four times or more with the operating air A, and the diluted sample gas S is oxidized by the oxidizing catalyst to remove the nonmethane hydrocarbons. The portion of hydrogen gas F, added at this time, serves to stabilize an oxidizing action of the cutter 6, and thus improve efficiency. In addition, it is preferable that a flow rate of the total gas flowing through the cutter 6 is set at about 1 liter/min and a concentration of oxygen within the cutter 6 is set at 15% by volume or more.

The sample gas S, diluted and oxidized in the above-described manner, is regulated in pressure by the fine regulation valve 7. It is then supplied to the FID 1 to be burnt, under the condition that the hydrogen gas and the operating air A are supplied into the FID 1, whereby conducting an appointed analysis.

Furthermore, in the case where the sample gas S has been previously diluted, it is sufficient that the pipe 18 is eliminated or a valve (not shown) is closed to prevent supplying the cutter 6 with the operating air A or the quantity of air is reduced by means of the flow controller 17.

According to the present invention, the measurement can be achieved not only in the case where the sample gas is diluted, but also in a so-called direct measurement procedure in which the raw sample gas is measured. Since a part of the operating air supplied to the FID is also supplied to the FID as air used for diluting the raw sample gas, the analyzer construction is not complicated and is inexpensive.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a methane analyzer system including a cutter chamber for preparing a sample gas prior to submission of the sample gas to a hydrogen flame ionization detector, the improvement comprising:
   a source of dilution gas connected to the hydrogen flame ionization detector; and
   means for directing a portion of the dilution gas to the cutter for mixing with the sample gas.

2. The invention of claim 1, wherein the means for directing includes a flow controller system.

3. The invention of claim 1, wherein the sample gas is supplied to the cutter by a supply line having a pressure regulator and a bypass line.

4. The invention of claim 1, further including a fuel gas supply connected to the hydrogen flame ionization detector and means for directing a portion of the fuel gas to the cutter.

5. The invention of claim 4, further including a flow controller for regulating the fuel gas supply to the cutter.

6. methane analyzer system comprising:
a supply line connected to a sample gas;
a source of oxygen;
a source of fuel;
a cutter connected to the sample gas supply line;
a hydrogen flame ionization detector connected to the cutter and the source of oxygen and source of fuel;
means for directing a portion of the oxygen from the oxygen source to the cutter for dilution of the sample gas; and
means for regulating the flow of oxygen from the source of oxygen upstream from both the directing means and the hydrogen flame ionization detector, whereby a correct portion of oxygen is finally delivered to the hydrogen flame ionization detector directly from the source of oxygen and indirectly through a dilution of the sample gas in the cutter.

7. The analyzer system of claim 6, further including a pressure regulator and a bypass line connected to the supply line.

8. The analyzer system of claim 6, wherein the means for regulating includes a flow controller valve and the means for directing includes a flow restrictor.

9. The analyzer system of claim 6, further including means for directing a portion of the fuel from the fuel source to the cutter.

10. methane analyzer system comprising:
a supply line connected to a sample gas;
a source of oxygen;
a source of fuel;
a cutter connected to the sample gas supply line;
a hydrogen flame ionization detector connected to the cutter and the source of oxygen and source of fuel;
first means for directing a portion of the oxygen from the oxygen source to the cutter for dilution of the sample gas;
second means for directing a portion of the fuel from the fuel source to the cutter to stabilize the oxidation of the sample gas by the cutter;
means for regulating the flow of oxygen from the source of oxygen upstream from both the directing means and the hydrogen flame ionization detector, whereby a correct portion of oxygen is finally delivered to the hydrogen flame ionization detector directly from the source of oxygen and indirectly through a dilution of the sample gas in the cutter; and
means for regulating the flow of fuel from the source of fuel upstream from both the second directing means and the hydrogen flame ionization detector, whereby a correct portion of fuel is finally delivered to the hydrogen flame ionization detector directly from the source of fuel and indirectly through the cutter.

11. The analyzer system of claim 10, wherein the means for regulating fuel and oxygen includes a flow restrictor.

* * * * *